United States Patent [19]

Agouridas et al.

[11] Patent Number: 5,786,339

[45] Date of Patent: *Jul. 28, 1998

[54] ERYTHROMYCINS

[75] Inventors: Constantin Agouridas; Jean-François Chantot, both of Nogent Sur Marne, France

[73] Assignee: Roussel Uclaf, France

[*] Notice: The term of this patent shall not extend beyond the expiration date of Pat. No. 5,543,400.

[21] Appl. No.: 565,252

[22] Filed: Nov. 30, 1995

[30] Foreign Application Priority Data

Dec. 9, 1994 [FR] France ................... 94 14807

[51] Int. Cl.⁶ ..................... A61K 31/70; C07H 17/08
[52] U.S. Cl. ............... 519/30; 536/7.2; 536/7.3; 536/7.4
[58] Field of Search ............... 536/29, 32, 7.3, 536/7.9, 7.2; 519/30

[56] References Cited

U.S. PATENT DOCUMENTS

| | | | |
|---|---|---|---|
| 5,527,780 | 6/1996 | Agouridas et al. | 514/29 |
| 5,543,900 | 8/1996 | Agouridas et al. | 519/29 |

FOREIGN PATENT DOCUMENTS 0606062   7/1994   European Pat. Off. .

*Primary Examiner*—Elli Reselev
*Attorney, Agent, or Firm*—Bierman, Muserlian & Lucas

[57] ABSTRACT

A compound selected from the group consisting of a compound of the formula

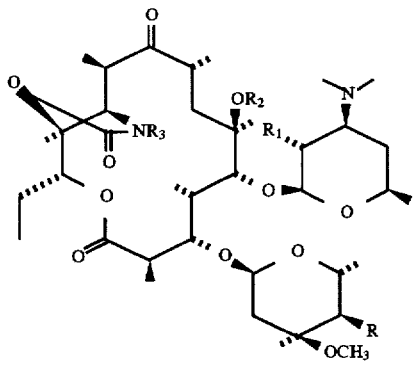

wherein R and $R_1$ are —OH or —O-acyl of an organic carboxylic acid of 2 to 20 carbon atoms, $R_2$ is hydrogen or methyl, $R_3$ is —$(CH_2)_m$—$R_4$ or

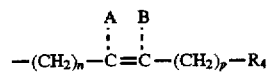

or —N—$(CH_2)_q$—$R_4$. m is an integer from 1 to 6, n, p and q are individually an integer from 0 to 6, A and B are individually selected from the group consisting of hydrogen, halogen and alkyl of 1 to 8 carbon atoms with the geometry of the double bond being E or Z or a mixture of E and Z or A and B form a triple bond, $R_4$ is an optionally substituted mono- or polycyclic heterocycle and their non-toxic, pharmaceutically acceptable acid addition salts having antibiotic properties.

23 Claims, No Drawings

ERYTHROMYCINS

OBJECTS OF THE INVENTION

It is an object of the invention to provide the novel compounds of formula I and their acid addition salts and a process and intermediate for their preparations.

It is another object of the invention to provide novel antibiotic compositions and a method of combatting bacterial infections in warm-blooded animals.

These and after objects and advantages will become obvious from the following detailed description.

THE INVENTION

The novel erythromycins of the invention are compounds selected from the group consisting of a compound of the formula

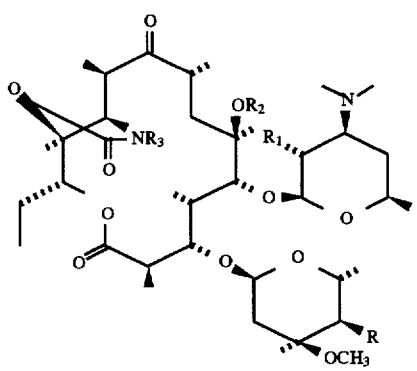

wherein R and $R_1$ are —OH or —O-acyl of an organic carboxylic acid of 2 to 20 carbon atoms, $R_2$ is hydrogen or methyl, $R_3$ is —$(CH_2)_m$—$R_4$ or

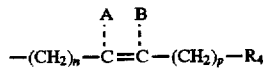

or —N—$(CH_2)_q$—$R_4$, m is an integer from 1 to 6, n, p and q are individually an integer from 0 to 6, A and B are individually selected from the group consisting of hydrogen, halogen and alkyl of 1 to 8 carbon atoms with the geometry of the double bond being E or Z or a mixture of E and Z or A and B form a triple bond, $R_4$ is an optionally substituted mono- or polycyclic heterocycle and their non-toxic, pharmaceutically acceptable acid addition salts.

Examples of acids, for the formation of the non-toxic, pharmaceutically acceptable acid addition salts are acetic acid, propionic acid, trifluoroacetic acid, maleic acid, tartaric acid, methanesulfonic acid, benzenesulfonic acid, p-toluenesulfonic acid, hydrochloric acid, hydrobromic acid, hydroiodic acid, sulfuric acid, phosphoric acid and especially stearic acid, ethylsuccinic acid and laurylsulfonic acid.

Examples of acyl are acetyl, propionyl, butyryl, isobutyryl, n-valeryl, isovaleryl, tert-valeryl, pivalyl or phenylmethoxycarbonyl.

The heterocycle contains one or more heteroatoms, preferably chosen from oxygen, sulfur and nitrogen. Examples of heterocycles with 5 members are preferably thienyl, furyl, pyrolyl, thiazolyl, oxazolyl, imidazolyl, thiadiazolyl, pyrazolyl, isoxazolyl or triazolyl and example of those with 6 members are preferably pyridyl, pyrimidinyl, pyridazinyl or pyrazinyl. The heterocycle can also be condensed such as benzimidazolyl, indolyl, benzofuranyl, benzothiazolyl or quinolinyl.

When the heterocycle is substituted, it is preferably by at least one substituent selected from the group consisting of halogen, hydroxy, alkyl, alkoxy, aryl and aryloxy containing up to 18 carbon atoms.

Among the preferred compounds of formula I are those wherein R and $R_1$ are hydroxy, those wherein $R_2$ is methyl, those wherein $R_3$ is —$(CH_2)_m$—$R_4$ and especially when m is 4 and those wherein $R_3$ is —N—$(CH_2)_q$—$R_4$ and especially when q is 3. $R_4$ is preferably a hetero-cycle with at least one ring nitrogen atom such as an optionally substituted imidazolyl, pyridinyl, thiazolyl, quinolinyl or azabenzimidazolyl, and more especially 4-phenyl-1H-imidazolyl or 4-quinolinyl. Specific preferred compounds are those of Examples 1, 2, 3 and 4.

The novel process for the preparation of the compounds of formula I comprises reacting a compound of the formula

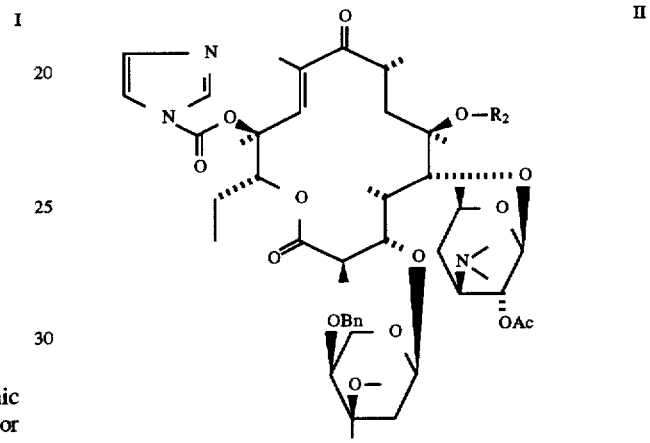

wherein $R_2$ is defined as above, Bn is benzyloxycarbonyl and Ac is an acyl radical as defined above with a compound of the formula

wherein $R_3$ is defined as above to obtain a compound of the formula

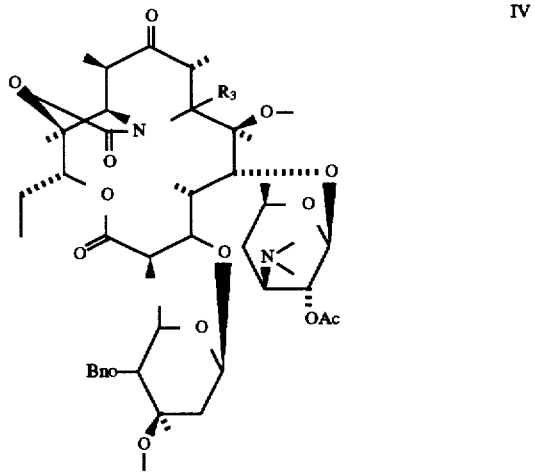

optionally subjecting the latter to the action of an agent which cleaves the 2'-ester function to obtain the compound of formula I in which $R_1$ is OH, then optionally subjecting the latter to the action of a reduction agent to cleave the 4"-benzyloxycarbonyl to obtain the product of formula I in which R is OH, then optionally subjecting the latter to the action of an acid to form the corresponding salt.

The compounds of formula II used as starting products are known products described in European Patent 0.248.279 and the amines of formula III are generally known and can be prepared by the processes described in J. Med. Chem. (1982), Vol. 25, p. 947 and subsequent or Tetrahedron Letters, Vol. 32, No. 14, pp. 1699, 1702 (1991).

The cleavage of the 2'-acetate is carried out using methanol or aqueous hydrochloric acid and the cleavage of the 4"-benzyloxycarbonyl is carried out by reduction, for example by means of hydrogen in the presence of a palladium catalyst. The salification is carried out with an acid by standard processes.

The compounds of formula I in which R is —N(CH$_2$)$_q$R$_4$ can be prepared by the action of hydrazine hydrate on the product of formula II to obtain the compound of formula P, that is to say a product of formula I, in which R$_3$ is NH$_2$, which is subjected to the action of an aldehyde R$_4$(CH$_2$)$_{q-1}$CHO to obtain the corresponding compound of formula I. The compound of formula P is a product of the invention as a new chemical product.

The antibacterial compositions of the invention are comprised of an antibacetericidally effective amount of at least one compound of formula I and their non-toxic, pharmaceutically acceptable acid addition salts and an inert pharmaceutical carrier. The compositions may be in the form of tablets, dragees, capsules, granules, suppositories, creams, gels, ointments and injectable solutions or suspensions.

The compositions of the invention have a very good antibiotic activity against gram ⊕ bacteria such as staphylococci, streptococci, pneumoccocci and can therefore be used in the treatment of infections caused by susceptible germs and particularly staphylococcal infections, such as staphylococcal septicemias, malignant staphylococcal infections of the face or skin, pyodermatitis, septic or suppurating wounds, boils, anthrax, phlegmons, erysipelas and acne, staphylococcal infections such as acute primary or post-influenzal angina, bronchopneumonia, pulmonary suppuration, streptococcal infections such as acute anginas, otitis, sinusitis, scarlet fever, pneumococcal infections such as pneumonia,, bronchitis; brucellosis, diphtheria and gonococcal infection.

The compositions of the invention are also active against infections caused by germs such as *Haemophilus influenzae*, *Moraxella catarrhalis*, Rickettsies, *Mycoplasma pneumoniae*, Chlamydia, Legionella, Ureaplasma, Toxoplasma or by germs of the Mycobacterium genus.

Examples of inert carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions can also be presented in the form of a powder intended to be dissolved extemporaneously in an appropriate vehicle, for example apyrogenic sterile water.

The method of the invention for treating bacterial infections in warm-blooded animals, including humans, comprises administering to warm-blooded animals an antibactericidally effective amount of a compound of formula I or its non-toxic, pharmaceutically acceptable acid addition salts. The compound may be administered orally, rectally, parenterally or topically and the usual daily dose is 0.6 to 4 mg/kg depending on the condition treated, the specific compound and the method of treatment.

In the following examples, there are described several preferred embodiments to illustrate the invention. However, it should be understood that the invention is not intended to be limited to the specific embodiments.

EXAMPLE 1

11,12-dideoxy-6-O-methyl-12,11-(oxycarbonyl-((4-(4-phenyl-1H-imidazol-2-yl)-butyl)-imino))-erythromycin a) Condensation 3 g of 10, 11-didehydro-11-deoxy-6-O-methyl-erythromycin-2'-acetate-12-(1H-imidazole-1-carboxylate)-4"-(phenylmethylcarbonate) in solution in 8.5 ml of acetonitrile and 0.85 ml of water were stirred with 2.5 g of 4-(4-phenyl-1H-imidazol-2-yl)-butyl amine for 5 minutes at ambient temperature, then for 16 hours at 80° C. After dilution with methylene chloride, the organic phase was washed with water, dried, filtered and the filtrate was evaporated of dryness to obtain 2.4 g of condensation product.

b) Deacetylation 2.4 g of the product of Stage a) in 50 ml of methanol were stirred for 16 hours. After evaporating to dryness, 2 g of product deacetylated in position 2' were obtained.

c) Hydrogenolysis

The product of Stage b was taken up in 60 ml of methanol and hydrogenated in the presence of 500 mg of 10% palladium on activated charcoal, followed by filtering, rinsing with methanol and concentrating to obtain 1.9 g of product which was chromatographed on silica eluting with an ethyl acetate - triethylamine mixture (95-5) to obtain 988 mg of the desired product.

| Microanalysis | Calculated | Found |
|---|---|---|
| C % | 64.31 | 64.2 |
| H % | 8.51 | 8.4 |
| N % | 5.77 | 5.7 |

| Mass spectrum | | |
|---|---|---|
| 971$^+$ = MH$^+$ | | |
| 158$^+$ = desosamine | | |

| IR: CHCl$_3$ | | |
|---|---|---|
| OH region | | 3610 – 3548 cm$^{-1}$ |
| $\diagdown_{C=O}\diagup$ | | 1732 – 1710 cm$^{-1}$ |
| Conjugated system + Aromatic | | 1605 – 1553 – 1500 cm$^{-1}$ |

| NMR: CDCl$_3$ 300 MHz ppm | | |
|---|---|---|
| CH$_3$—CH$_2$ | | 0.81 (t) |
| CH$_3$—CH | | 1.01 (d)–1.11 (d)–1.14 (d) |
| | approx. | 1.22 (m)–1.30 (d) |
| the CH$_3$—C— 's | | 1.26 (s)–1.40 (s) x 2 |
| N(CH$_3$)$_2$ | | 2.28 (s) |
| H'$_3$ | approx. | 2.40 (m) |
| H$_4$ | | 2.60 (m) |
| H$_2$ | | 2.92 (m) |
| O—CH$_3$ in position 6 | | 3.01 (s) |
| H"$_4$ | approx. | 3.05 |
| H$_{10}$ | | 3.11 (wq) |
| H'$_2$ | | 3.18 (dd) |
| O—CH$_3$ in position 3" | | 3.33 (s) |
| H'$_5$ | | 3.48 (m) |

| | | |
|---|---|---|
| H₁₁ | | 3.63 (s) |
| H₃, H₅ and CH₂NC=O | | 3.60 to 3.85 |
| H"₅ | approx. | 4.00 (m) |
| CH₂NC= | | 4.02 (t) |
| H'₁ | | 4.43 (d) |
| H"₁ | | 4.90 (d) |
| H₁₃ | | 4.95 (dd) |
| H in para position | | 7.20 |
| H in meta position | | 7.34 phenyl |
| H in ortho position | | 7.76 |
| H₂ | | 7.52 (d) imidazole |
| H₅ | | 7.26 (d) |

EXAMPLE 2

11,12-dideoxy-6-O-methyl-12,11-(oxycarbonyl-(4-(4-quinolinyl)-butyl)-imino))-erythromycin (product A) and

EXAMPLE 3

11,12-dideoxy-6-O-methyl-12,11-(oxycarbonyl-(4-(1,2,3,4-tetrahydro)-4-quinolinyl)-butyl)-imino))-erythromycin (product B)

A mixture of 3 g of 10,11-didehydro-11-deoxy-6-O-methylerythromycin-2'-acetate-12-(1H-imidazole-1-carboxylate)-4"-(phenylmethylcarbonate) in 8.5 ml of acetonitrile and 0.85 ml of water and 2.4 g of 4-(4-quinolinyl) butylamine were stirred for 5 minutes at ambient temperature, then for 24 hours at 80° C., followed by diluting with methylene chloride, washing, drying, filtering and evaporating to dryness to obtain 4 g of product which was purified by chromatography eluting with a methylene chloride - methanol mixture (98-2) to obtain 2 g of the desired condensation product.

b) Deacetylation 2 g of the product of Stage a) were taken up in 200 ml of methanol and the mixture was stirred for 16 hours, followed by evaporation to dryness to obtain the deacetylated crude product.

c) Hydrogenolysis 2 g of the product of Stage b) in solution in methanol were hydrogenated for 4 hours in the presence of 1 g of 10% palladium on activated charcoal, followed by filtering, rinsing with methanol and evaporation to dryness. Chromatography was carried out on silica eluting with a methylene chloride - methanol, ammonium hydroxide mixture (95-5-03). 2 fractions were recovered: 712 mg of product A and 320 mg of product B in the form of 1,2,3,4-tetrahydroquinoline.

Fraction A:

The 712 mg of product A were crystallized from a methanol water mixture. After separating, washing with a methanol - water mixture and drying at 60° C., 490.6 mg of the expected product A were obtained melting at 230° C.

| Microanalysis | Calculated | Found |
|---|---|---|
| C % | 65.32 | 65.1 |
| H % | 8.54 | 8.7 |
| N % | 4.39 | 4.4 |

Mass spectrum 956.3 = MH⁺

NMR: CDCl₃ 300 MHz ppm

| | | |
|---|---|---|
| CH₃—CH₂ | | 0.78 (t) |
| CH₃—CH | | 1.01 (d)-1.11 (d)-1.13 (d) |
| | | 1.23 (d x 2)-1.32 (d) |
| the CH₃—C— 's | | 1.27 (s)-1.39 (s x 2) |
| N(Me)₂ | | 2.29 (s) |
| H'₃ | approx. | 2.38 |
| H₈ | | 2.58 (m) |
| 6-OMe | | 2.96 (s) |
| H₁₀, H'₂, H"₄, CH₂C= | | 3.00 to 3.25 |
| 3"-OMe | | 3.33 (s) |
| H'₅ (in excess) | | 3.48 (m) |
| H₁₁ | | 3.63 (s) |
| H₃, H₅ and CH₂NC=O | | 3.6 to 3.85 |
| H"₅ | | 4.01 (m) |
| H'₁ | | 4.43 (d) |
| H₁₃ | | 4.93 (dd) |
| H"₁ | approx. | 4.96 |
| H₆ and H₇ | | 7.53–7.67 (dt) |
| H₃ | approx. | 7.26 quinoline |
| H₅ and H₈ | approx. | 8.07 (d) |
| H₂ | | 8.78 (d) |

Fraction B:

320 mg of product B were suspended in 30 ml of methanol, followed by filtering, washing with methanol and drying at 50° C. to obtain 113.8 mg of product which was dissolved in methylene chloride, filtered, then evaporated to dryness to obtain 70 mg of the expected product B melting at >260° C.

| Microanalysis | Calculated | Found |
|---|---|---|
| C % | 65.04 | 65.0 |
| H % | 8.92 | 9.1 |
| N % | 4.38 | 4.2 |

Mass spectrum 960.8 = MH⁺

NMR: CDCl₃ 300 MHz ppm

| | | |
|---|---|---|
| CH₃—CH₂ | | 0.83 (wt) |
| CH₃—CH | | 1.02 (d)-1.11 (d)-1.13 (d) |
| | approx. | 1.23–1.31 (d) |
| the CH₃—C— 's | | 1.26–1.39–1.40 |
| N(Me)₂ | | 2.29 (s) |
| H'₃ | approx. | 2.39 (m) |
| H₈ | | 2.59 (m) |
| H₂, H₁₀, H'₂, | | 2.65 to 3.35 |
| the 6-OMe's | | 3.02 and 3.03 |
| 3"-OMe | | 3.33 (s) |
| H'₅ | | 3.49 (m) |
| H₁₁ | | 3.64 (s) |
| H₃, H₅ and CH₂NC=O | | 3.60 to 3.80 |
| H"₅ | | 4.00 (m) |
| H'₁ | | 4.43 (d) |
| H"₁ | | 4.91 (d, resolved) |
| H₁₃ | | 4.98 (dd, resolved) |
| H₅ | | 6.46 (d) |
| H₈ | | 7.04 (d) |
| H₆ and H₇ | | 6.60 (m) and 7.94 (t) |

EXAMPLE 4

11,12-dideoxy-6-O -methyl-12,11-(oxycarbonyl-(2-(3-(4-quinolinyl)-propyl)-hydrazono)-erythromycin STAGE A: Preparation of 11,12-dideoxy-6-0-methyl-12,11-oxycarbonyl-(2-hydrazono))-erythromycin (product P)

a) Condensation

A mixture of 3 g of 10,11-didehydro-11-deoxy-6-O-methylerythromycin-2'-acetate-12-(1H-imidazole-1-carboxylate-4"-(phenylmethylcarbonate), 3 ml of hydrazine hydrate, 30 ml of acetonitrile and 492 mg of caesium carbonate were plunged into a bath at 80° C. for 10 minutes, followed by concentrating to dryness, taking up in methylene chloride, washing with water, drying, filtering and bringing to dryness.

b) Deacetylation

The 3 g of product were dissolved in 30 ml of methanol and the mixture was stirred at ambient temperature for 15 hours. The reaction medium was concentrated to dryness to obtain 2.7 g of the deacetylated product.

c) Hydrogenolysis

The product of Stage b) was dissolved in 100 ml of methanol and hydrogenation was carried out in the presence of 600 mg of 10% palladium on activated charcoal, followed by filtering, rinsing with methanol and with methylene chloride. Then, the filtrate was concentrated to dryness to obtain 2.52 g of a product which was purified by eluting with an isopropyl ether - methanol - triethylamine mixture (80-10-10) to obtain 941.8 mg of a product which was chromatographed again eluting with an isopropyl ether-methanol-triethylamine mixture (80-10-10) to obtain 761 mg of 6-O-methyl-12,11-(oxycarbonyl)-(2-hydrazono))-erythromycin.

| Microanalysis | Calculated | Found |
|---|---|---|
| C % | 59.45 | 58.8 |
| H % | 8.83 | 8.5 |
| N % | 5.33 | 5.2 |

Mass spectrum $788^+ = MH^+$
$810^+ = MNa^+$

NMR: CDCl$_3$ 300 MHz ppm

| | |
|---|---|
| CH$_3$—CH$_2$ | 0.84 (t) |
| the CH$_3$—CH's | 1.08 (d)–1.11 (d)–1.14 (d) |
| | 1.16 (d)–1.21 (d)–1.23 (d) |
| the CH$_3$—C— 's | 1.26 (s)–1.38 (s)–1.41 (s) |
| N(Me)$_2$ | 2.28 (s) |
| H'$_3$ | approx. 2.40 (m) |
| H$_2$ | 2.88 (m) |
| H$_8$ | 2.66 (m) |
| H"$_4$ | approx. 3.00 |
| the 6-OMe's | 3.02 (s) |
| H$_{10}$ | approx. 3.08 (m) |
| H'$_2$ | 3.18 (dd) |
| 3"-OMe | 3.33 (s) |
| H'$_5$ | 3.48 (m) |
| H$_{11}$ | 3.60 (s) |
| H$_3$ and H$_5$ | 3.65 (d) |
| H"$_5$ | 4.00 (m) |
| H"$_1$ | 4.43 (d) |
| H$_{12}$ | 4.50 (s) |
| H"$_1$ | 4.91 (d) |
| H$_{13}$ | 5.02 (dd) |

STAGE B: 11,12-dideoxy-6-O-methyl-12,11-(oxycarbonyl-(2-(3-(4-quinolinyl)-propyl)-hydrazono)-erythromycin A mixture of 230 mg of the product of Stage A, 5 ml of methanol, 0.3 g of quinoline 4-propanal, 0.055 ml of acetic acid was stirred for 15 hours at ambient temperature. 0.065 g of sodium cyanoborohydride were added followed by stirring at ambient temperature for 24 hours. The methanol was evaporated off, followed by extraction with ethyl acetate, washing with sodium hydroxide solution, then with water, drying, filtering and evaporating to dryness to obtain 220 mg of a product which was chromatographed on silica eluting with an ethyl acetate - triethylamine mixture (95-5) to obtain 80 mg of the desired product.

| Microanalysis | Calculated | Found |
|---|---|---|
| C % | 63.99 | 64.1 |
| H % | 8.42 | 8.3 |
| N % | 5.85 | 5.7 |

Mass spectrum $158^+ = $ OH in position 2'
$957^+ = (M + H)^+$
$979^+ = (M^+Na)^+$ NMR: CDCl$_3$ 400 MHz ppm

| | | |
|---|---|---|
| CH$_3$-15 | | 0.78 (t) |
| CH$_3$-10 | | 1.07 (d) |
| CH$_3$-4 | | 1.11 (d) |
| CH$_3$-8 | | 1.16 (d) |
| CH$_3$-5' and CH$_3$-2 | | 1.22 (d) |
| CH$_3$-5" | | 1.32 (d) |
| the CH$_3$—C— 's | | 1.26 (s)–1.38 (s)–1.40 (s) |
| CH$_2$-14 | | 1.52 (m) - approx. 1.90 (m) |
| CH$_2$-2" | | 1.62 (dd, J=15 and 5) |
| | | 2.38 (d, J=15) |
| H$_4$ | approx. | 1.87 (m) |
| OH-4" | | 2.20 (wide, mobile d) |
| N(CH$_3$)2 | | 2.29 (s) |
| H'$_3$ | | 2.42 (m) |
| H$_8$ | | 2.65 (m) |
| H$_2$ | | 2.94 (m) |
| OCH$_3$-6 | | 2.99 (s) |
| H"$_4$ | | 3.03 (m) |
| H$_{10}$ and H'$_2$ | approx. | 3.17 (m) |
| OCH$_3$-3" | | 3.33 (s) |
| CH$_2$—O and CH$_2$—N | | 2.90 to 3.35 (m) |
| H'$_5$ | | 3.49 (m) |
| H$_5$ | | 3.67 (d, J=7) |
| H$_3$ | | 3.70 (d, J=10) |
| H$_{11}$ | | 3.76 (s) |
| H"$_5$ | | 4.01 (m) |
| H'$_1$ | | 4.43 (d, J=7) |
| H"$_1$ | | 4.94 (wd, J=5) |
| H$_{13}$ | | 4.98 (dd, J=11 and 2) |
| NH—CH$_2$ | | 5.63 (m, mobile) |
| H$_3$ | | 7.30 (d, J=4) |
| H$_2$ | | 8.78 (d, J=4) |
| H$_6$, H$_7$ | | 7.52 (dt)–7.66 (dt) |
| H$_5$, H$_8$ | | 8.07 (wd)–8.12 (wd) |

EXAMPLE 5

11,12-dideoxy-6-O-methyl-12,11-(oxycarbonyl-((4-(3H-imidazo[4,5-b]pyridin-3-yl)-butyl)-imino))-erythromycin a) Condensation A mixture of 3 g of 10,11-didehydro-11-deoxy-6-O-methylerythromycin-2'-acetate-12-(1H-imidazole-1-carboxylate)-3'-phenylmethylcarbonate) and 2.2 g of 4-(3H-imidazo[4,5-b] pyridin-3-yl-butylamine in 8.42 ml of acetonitrile and 0.85 ml of water was stirred for 5 minutes at ambient temperature, then for 16 hours at 80° C. The reaction medium was diluted with 50 ml of methylene chloride, washed with salt water, filtered and evaporated to dryness to obtain 4.1 g of product which was chromatographed on silica eluting with a methylene chloride - methanol - ammonium hydroxide mixture (95-5-0.4).

b) Deacetylation

The product of Stage a was stirred at ambient temperature for 16 hours with 50 ml of methanol and after evaporation to dryness, 2.26 g of deacetylated product were obtained.

c) Hydrogenation

The product of Stage b was taken up in 100 ml of methanol and hydrogenated in the presence of 1 g of 10% palladium on activated charcoal, followed by filtering, rinsing and bringing to dryness to obtain 1.58 g of product which was chromatographed on silica, eluant methylene chloride - methanol - ammonium hydroxide (95-5 0.5) to obtain 1.3 g of the desired product with a Rf=0.14.

| IR in CHCl$_3$ | | |
|---|---|---|
| OH | approx. | 3610 cm$^{-1}$ – 3550 cm$^{-1}$ |
| $\diagdown_{\diagup}$C=O | | 1740 – 1709 cm$^{-1}$ |
| Heteroatom | | 1601 – 1584 – 1501 cm$^{-1}$ |

| Mass spectrum | |
|---|---|
| 946$^{+}$/ = (M + H)$^+$ | |
| 952$^{+}$/ = (M$^+$Li)$^+$ | |

| NMR: CDCl$_3$ 300 MHz ppm | | |
|---|---|---|
| CH$_3$—CH$_2$ | | 0.83 (t) |
| the CH$_3$—CH's | | 1.00 (d)–1.10 (d)–1.13 (d) |
| | | 1.23 (d)x 2–1.32 (d) |
| the CH$_3$—C— 's | | 1.27 (s)–1.39 (s x 2) |
| N(Me)$_2$ | | 2.28 (s) |
| H'$_3$ | approx. | 2.39 (m) |
| H$_8$ | approx. | 2.59 (m) |
| H$_2$ | | 2.89 (m) |
| the 6-OMe's | | 2.92 (s) |
| H$_{10}$ and H"$_4$ | approx. | 3.06 |
| H'$_2$ | | 3.18 (dd) |
| 3"-OMe | | 3.33 (s) |
| H'$_5$ | approx. | 3.48 (m) |
| H$_{11}$ | | 3.62 (s) |
| H$_3$, H$_5$ and CH$_2$—NC=O | | 3.6 to 3.85 |
| H"$_5$ | | 4.01 (m) |
| CH$_2$—NC= | approx. | 4.37 (m) |
| H"$_1$ and H$_{13}$ | approx. | 4.93 |
| H$_5$ | | 7.21 (dd) |
| H$_4$ | | 8.04 (dd) |
| H$_6$ | | 8.38 (dd) |
| H$_2$ | | 8.12 (s) |

EXAMPLE 6

11,12-dideoxy-6-O-methyl-12,11-(oxycarbonyl-((4-(1H-imidazol-1-yl)-butyl)-imino))-erythromycin a) Condensation A mixture of 10,11-dehydro-11-deoxy-6-O-methyl-erythromycin-2'-acetate-12-(1H-imidazole-1-carboxylate)-4"-(phenylmethylcarbonate) and 1.2 g of 4-(1H-imidazol-1-yl)-butylamine in 10 ml of acetonitrile and 1 ml of water was heated at 50° C. for 15 hours, followed by diluting with methylene chloride, washing with salt water, drying and evaporating to dryness to obtain 5.2 g of a product which was chromatographed on silica eluting with an ethyl acetate -methanol mixture (95-5) to obtain 1.19 g of product.

b) Deacetylation and hydrogenolysis 1.1 g of the product of Stage a) were dissolved in 110 ml of methanol degassed beforehand by bubbling nitrogen through it. 550 mg of 10% palladium on charcoal were added and the suspension obtained was vigorously stirred under 1600 mb of hydrogen pressure. After 35 minutes, filtration was carried out on clarcel, followed by rinsing with methanol and evaporating to dryness to obtain 930 mg of product which was taken up in methanol and stood for 16 hours at ambient temperature. After evaporating to dryness and chromatographing on silica, eluting with CH$_2$Cl$_2$ 95, MeOH 5, NH$_4$OH 0.5, 587 mg of purified product were obtained to which was added 547 mg from a precedent batch and the whole was taken up in methylene chloride. The solution was filtered and then the solvent was evaporated off under reduced pressure to obtain 1.13 g of the expected product with a Rf=0.2 (ethyl acetate 90, MeOH 5, TEA 5).

| Microanalysis | Calculated | Found |
|---|---|---|
| C % | 61.72 | 61.4 |
| H % | 8.78 | 9.0 |
| N % | 6.26 | 6.0 |

| NMR: CDCl$_3$ 300 MHz ppm | | |
|---|---|---|
| CH$_3$—CH$_2$ | | 0.83 (t) |
| the CH$_3$—CH's | | 1.00 (d)–1.11 (d)–1.13 (d) |
| | | 1.23 (d)x 2–1.32 (d) |
| the CH$_3$—C— 's | | 1.26–1.39–1.41 |
| N(Me)$_2$ | | 2.28 (s) |
| H'$_3$ | approx. | 2.38 (m) |
| H$_8$ | approx. | 2.60 (m) |
| H$_2$ | | 2.92 (m) |
| the 6-OMe's | | 3.00 (s) |
| H"$_4$ | approx. | 3.03 (t) |
| H$_{10}$ | | 3.03 (wq) |
| H'$_2$ | | 3.19 (dd) |
| 3"-OMe | | 3.33 (s) |
| H$_{11}$ | | 3.62 (s) |
| H$_3$, H$_5$, H'$_5$ and CH$_2$—NC=O | | 3.55 to 3.80 |
| CH$_2$—NC= | | 3.99 (t) |
| H"$_5$ | | 4.04 (m) |
| H'$_1$ | | 4.43 (d) |
| H"$_1$ and H$_{13}$ | | 4.93 (m) |
| H$_4$ and H$_5$ | | 6.93 (t)–7.02 (ws) imidazole |
| H$_2$ | | 7.48 (ws) |

Using the procedure of the above examples, the following products were prepared:

EXAMPLE 7

11,12-dideoxy-6-O-methyl-12,11-(oxycarbonyl-((4-(4-(3-pyridinyl)-1H-imidazol-1-yl)-butyl)-imino))-erythromycin.

EXAMPLE 8

11,12-dideoxy-6-O-methyl-12,11-(oxycarbonyl-(2-(3-(4-phenyl-1H-imidazol-1-yl)-propyl)-hydrazono-erythromycin with a Rf=0.1 (isopropyl ether-methanol-triethylamine 80-10-10).

EXAMPLE 9

6-O-methyl-12,11-(oxycarbonyl-(2-(3-(3H-imidazo (4,5-b)-pyridin-3-yl)-propyl)-hydrazono))-erythromycin with a Rf=0.2 (isopropyl ether-methanol-triethylamine 80-10-10).

EXAMPLE 10

6-O-methyl-12,11-(oxycarbonyl-(2-(3-(2-phenyl-4-thiazolyl)-propyl)-hydrazono))-erythromycin with a Rf=0.14 (isopropyl ether-methanol-triethylamine 80-10-10).

EXAMPLES OF PHARMACEUTICAL COMPOSITIONS

Tablets were prepared containing 150 mg of the product of Example 1 or 2A or 4 and sufficient excipient of starch, talc and magnesium stearate for a final weight of 1 gram.

PHARMACOLOGICAL STUDY

Method of dilutions in liquid medium

A series of tubes were prepared into which the same quantity of sterile nutritive medium was distributed and increasing quantities of the product to be studied were distributed into each tube. Then, each tube was seeded with a bacterial strain and after incubation for twenty-four hours in a heating chamber at 37° C., the growth inhibition was evaluated by transillumination which allowed the minimal inhibitory concentrations (M.I.C.) to be determined, expressed in micrograms/ml. The results were reported in the following Table.

| Products | GRAM⁺ BACTERIAL STRAINS | | | |
|---|---|---|---|---|
| | Ex. 1 | Ex. 2 | Ex. 3 | Ex. 4 |
| Staphylococcus aureus 011UC4 | 0.15 | 0.15 | 0.6 | 0.3 |
| Streptococcus pyogenes group A 02A1UC1 | 0.04 | 0.04 | 0.04 | 0.08 |
| Streptococcus agalactiae group B 02B1HT1 | ≦0.02 | ≦0.02 | ≦0.02 | ≦0.02 |
| Streptococcus faecalis group D 02D2UC1 | 0.04 | 0.04 | 0.04 | 0.08 |
| Streptococcus faecium group D 02D3HT1 | 0.04 | 0.04 | 0.04 | 0.08 |
| Streptococcus sp group G 02G0GR5 | 0.04 | 0.04 | 0.04 | 0.08 |
| Streptococcus agalactiae group B 02B1SJ1 | 0.6 | 0.6 | 0.3 | 5 |

Various modification of the compounds and the method of the invention may be made without departing from the spirit or scope thereof and it is to be understood that the invention is intended to be limited only as defined in the appended claims.

What is claimed is:
1. A compound of the formula

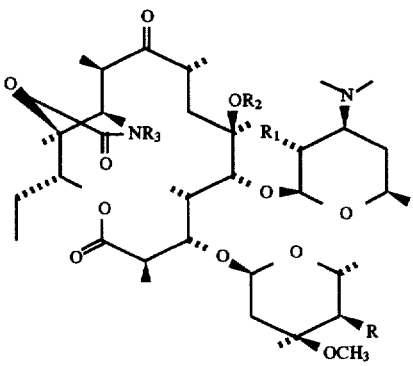

wherein R and $R_1$ are —OH or —O-acyl of an organic carboxylic acid of 2 to 2- carbon atoms, $R_2$ is hydrogen or methyl, $R_3$ is —$(CH_2)_m$—$R_4$ or

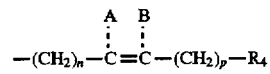

or —N—$(CH_2)_q$—$R_4$, m is an integer from 1 to 6 n, p and q are individually an integer from 0 to 6, A and B are individually selected from the group consisting of hydrogen, halogen and alkyl of 1 to 8 carbon atoms with the geometry of the double bond being E or Z or a mixture of E and Z or A and B form a triple bond, $R_4$ is selected from the group consisting of thienyl, furyl, pyrolyl, thiazolyl, oxazolyl, imidazolyl; 4-phenyl-1H-imidazolyl, thiadiazolyl, pyrazolyl, imidazo[4,5-b]-pyridin-3yl, triazolyl, pyridyl, pyrimidinyl, pyridazinyl, pyrazinyl, benzimidazolyl, indolyl, benzofuranyl, and quinolinyl, all optionally substituted with at least one substituent selected from the group consisting of halogen, hydroxy, alkyl, alkoxy, aryl and aryloxy containing up to 18 carbon atoms or a non-toxic, pharmaceutically acceptable acid addition salt thereof.

2. A compound of claim 1 wherein R and $R_1$ are —OH.
3. A compound of claim 1 wherein $R_2$ is methyl.
4. A compound of claim 1 wherein $R_3$ is —$(CH_2)_m R_4$.
5. A compound of claim 4 wherein m is 4.
6. A compound of claim 1 wherein $R_3$ is —N—$(CH_2)_q R_4$.
7. A compound of claim 6 wherein q is 3.
8. A compound of claim 1 wherein the heterocycle is selected from the group consisting of pyridyl, thiazolyl, quinolinyl, and optionally substituted imidazolyl.
9. A compound of claim 8 wherein $R_4$ is 4-phenyl-1H-imidazolyl or 4-quinolinyl.
10. A compound of claim 1 selected from the group consisting of
11,12-dideoxy-6-O-methyl-12,11-(oxycarbonyl-((4-(4-phenyl-1H-imidazol-2-yl)-butyl)-imino))-erythromycin,
11,12-dideoxy-6-O-methyl-12,11-(oxycarbonyl-((4-(4-quinolinyl)-butyl)-imino))-erythromycin,
11,12-dideoxy-6-O-methyl-12,11-(oxycarbonyl-(4-(1,2,3,4-tetrahydro)-4-quinolinyl)-butyl)-imino))-erythromycin and
11,12-dideoxy-6-O-methyl-12,11-[oxycarbonyl-(2-(3-(4-quinolinyl)-propyl)-hydrazono)]-erythromycin.
11. An antibiotic composition comprising an antibiotically effective amount of a compound of claim 1 and an inert pharmaceutical carrier.
12. A composition of claim 11 wherein the active compound is selected from the group consisting of
11, 12-dideoxy-6-O-methyl-12, 11-(oxycarbonyl-((4-(4-phenyl-1H-imidazol-2-yl)-butyl)-imino))-erythromycin,
11, 12-dideoxy-6-O-methyl-12, 11-(oxycarbonyl-((4-(4-quinolinyl)-butyl)-imino))-erythromycin,
11,12-dideoxy-6-O-methyl-12,11-[oxycarbonyl-(4-(1,2,3,4-tetrahydro)-4-quinolinyl)-butyl)-imino))-erythromycin and
11,12-dideoxy-6-O-methyl-12,11-(oxycarbonyl-(2-(3-(4-quinolinyl)-propyl)-hydrazono)]-erythromycin.
13. A method of combatting bacterial infections in warm-blooded animals comprising administering to warm-blooded animals an antibactericidally effective amount of a compound of claim 1.
14. A method of claim 13 wherein R and $R_1$ are —OH.
15. A method of claim 13 wherein $R_2$ is methyl.
16. A method of claim 13 wherein $R_3$ is —$(CH_2)_m$—$R_4$.
17. A method of claim 16 wherein m is 4.

18. A method of claim 13 wherein $R_3$ is —N—$(CH_2)_q$—$R_4$.

19. A method of claim 18 wherein q is 3.

20. A method of claim 13 wherein the heterocycle is selected from the group consisting of pyridyl, thiazolyl, quinolinyl, and optionally substituted imidazolyl.

21. A method of claim 13 wherein $R_4$ is 4-phenyl-1H-imidazolyl or 4-quinolinyl.

22. The method of claim 13 wherein the active compound is selected from the group consisting of 11,12-dideoxy-6-O-methyl-12,11-(oxycarbonyl-((4-(4-phenyl-1H-imidazol- 2-yl)-butyl)-imino))-erythromycin, 11,12-dideoxy-6-O-methyl-12,11-(oxycarbonyl-((4-(4-quinolinyl)-butyl)-imino))-erythromycin, 11,12-dideoxy-6-O-methyl-12,11-(oxycarbonyl-(4-(1,2,3,4-tetrahydro)-4-quinolinyl)-butyl)-imino))-erythromycin and 11,12-dideoxy-6-O-methyl-12,11-[oxycarbonyl-(2-(3-(4-quinolinyl)-propyl)-hydrazono)]-erythromycin.

23. 11,12-dideoxy-6-O-methyl-12,11-(oxycarbonyl)-(2-hydrazono)erythromycin.

* * * * *